| United States Patent [19] | [11] | 4,423,029 |
|---|---|---|
| Rizzi | [45] | Dec. 27, 1983 |

[54] (S)-3-AMINO-4-[(S,S)-1-(1-HYDROXYETHYL)ALKYL AMINO]-4-OXO-BUTYRIC ACID COMPOUNDS SUITABLE AS NON-NUTRITIVE SWEETNERS

[75] Inventor: George P. Rizzi, Cincinnati, Ohio

[73] Assignee: The Procter & Gamble Company, Cincinnati, Ohio

[21] Appl. No.: 277,307

[22] Filed: Jun. 25, 1981

[51] Int. Cl.$^3$ ............... C07C 101/30; A61K 7/22; A23L 1/236

[52] U.S. Cl. ............... 424/54; 260/501.11; 426/548; 426/590; 562/507; 562/564; 562/503

[58] Field of Search ............... 562/564, 503, 508; 424/54; 426/548, 590; 260/501.11

[56] References Cited

U.S. PATENT DOCUMENTS

| 3,803,223 | 4/1974 | Mazur | 562/561 |
|---|---|---|---|
| 3,971,822 | 7/1976 | Chibata | 562/564 |
| 4,338,346 | 7/1982 | Brand | 426/548 |

FOREIGN PATENT DOCUMENTS 851368 5/1977 Belgium .
1381826 1/1975 United Kingdom .

OTHER PUBLICATIONS

R. H. Mazur, J. M. Schlatter, A. H. Goldkamp, *JACS*, 91, 2684 (1969).
R. H. Mazur, A. H. Goldkamp, P. A. James, J. M. Schlatter, *J. Med. Chem.*, 13, 1217 (1970).
Y. Ariyoshi, N. Yasuda, K. Yamatani, *Bull. Chem. Soc. Japan*, 47, 326 (1974).
L. B. P. Brussel, H. C. Peer, A. van der Heijden, *Z. Lebensm. Unters. Forsch*, 159, 339 (1975).
M. Miyoshi, K. Nanami, H. Sugano, T. Fujii, *Bull. Chem. Soc. Japan*, 51, 1433 (1978).
E. F. Marsh, D. A. Herring, *J. Pharm. Exp. Therapy*, 102, 178 (1951).

*Primary Examiner*—Michael L. Shippen
*Attorney, Agent, or Firm*—Michael J. Roth; Eric W. Guttag; Richard C. Witte

[57] ABSTRACT

(S)-3-amino-4-[(S,S)-1-(1-hydroxyethyl)alkylamino]-4-oxo-butyric acid compounds are non-nutritive sweeteners having favorable chemical and physiological properties.

16 Claims, No Drawings

(S)-3-AMINO-4-[(S,S)-1-(1-HYDROXYETHYL)ALKYL AMINO]-4-OXO-BUTYRIC ACID COMPOUNDS SUITABLE AS NON-NUTRITIVE SWEETNERS

TECHNICAL FIELD

The most widely used natural sweetener for food and similar preparations is sucrose. Sucrose is safe, naturally occurring, and has a high sweetness quality, i.e., a pure, quick onset with no aftertaste or undertaste.

One drawback to the use of sucrose as a sweetener is its caloric content. Many persons who have excess weight use non-nutritive sweeteners because the use of sucrose contributes to weight gain rather than weight control or reduction. Persons who have diabetes must carefully control their intake of sugar to avoid problems associated with the disease.

A second drawback to sucrose is that it is cariogenic and therefore cannot be used in dentifrices and is undesirable in chewing gums. A third drawback is that sucrose does not have a sufficiently high sweetness intensity for some compositions, e.g. dentifrices. If enough sucrose is used to make the composition sweet, the product becomes tacky and hygroscopic. Additionally, for the amount of sweetness delivered, sucrose is expensive.

It can be appreciated that the search continues for compounds which have high sweetness intensity and quality, and are stable, non-nutritive, and safe for oral consumption.

Numerous compounds have been discovered which have a sweet taste. However, the development of a useful non-nutritive sweetener requires the simultaneous fulfillment of multiple criteria involving not only taste, but the chemical and toxicological characteristics of the compound.

In the area of taste, for example, a synthetic sweetener should have a clean, sucrose-like sweetness to be acceptable. The sweetness should have an onset and duration comparable to sucrose. Since most synthetic sweeteners are compounds not found in nature, sweetness intensity is preferably as high as possible, to minimize potential metabolic load and toxicologic exposure. If the compound has caloric value, or is metabolized to materials having caloric value, the highest possible sweetness intensity assures minimal caloric content for a given level of sweetness. At the same time, sweetness intensity should not be so high as to preclude convenient dilution in use to provide appropriate sweetness levels.

From a chemical standpoint, a non-nutritive sweetener ideally should be freely soluble in both aqueous and non-aqueous media intended for oral consumption or use. As a practical matter, many materials which are readily water soluble are only sparingly soluble in edible organic media, such as triglyceride oils, and vice versa. Generally, good aqueous solubility is acceptable, since most food, beverage, and dentifrice compositions are aqueous or partially aqueous in nature. It is also important that a non-nutritive sweetener be chemically stable in such compositions, and not react with the components of these compositions or break down in their presence. In addition, to the extent that a minor level of reactivity or breakdown occurs, the product of such reactions or breakdowns should be toxicologically safe and generate no undesirable off-flavors.

From a safety standpoint, a sweetener compound should have both low acute toxicity (i.e., high $LD_{50}$) and a high "no effect level" as demonstrated in long term feeding studies, be minimally absorbed into the bloodstream, and rapidly cleared therefrom. Any metabolism which occurs should yield toxicologically safe products which are readily eliminated. The potential of the compound for eliciting carcinogenic, mutagenic and teratogenic effects must be proven negative by appropriate animal tests.

Of course, safety is the sine qua non of any synthetic sweetener. It can be seen, though, that any of a number of factors can affect the utility of a potential non-nutritive sweetener candidate. Thus, the bitter aftertaste and questionable safety profile of a compound such as saccharin can be detrimental to public acceptance. The cyclamates have been banned by the Food and Drug Administration because they are thought to be carcinogenic or mutagenic; they are also low in sweetening power and have an undesirable aftertaste. Neohesperidin dihydrochalcone has a sweetness intensity over 900 times that of sucrose; however, the sweetness is slow to develop and it has a licorice-like aftertaste. Aspartame ®, a dipeptide, has a high quality sweetness of approximately 150 times sucrose, but its chemical structure is such that it hydrolyzes rapidly in aqueous media to non-sweet compounds. Aspartic acid derivatives of certain aliphatic amines are sweet but are hydrolyzed by enzymes in the gastrointestinal tract to release potent, pharmacologically active materials. Even for intensely sweet compounds, low solubility can limit the effective sweetening power of a compound to such an extent that insufficient sweetness can be imparted to systems such as foods, beverages and other compositions for oral use.

Non-nutritive sweeteners have been known for over one hundred years (saccharin, 1879) and theories have been proposed to account for the perception of sweetness and the chemical structures that produce that perception. Yet there seems to be no common molecular property which can be used to predict either the level or, especially, the quality of sweetness. Ingenious models have been proposed to explain the sweetness of known compounds, but not all compounds fitting the models are sweet and the theories cannot be used to predict or construct new sweeteners. The essential structural determinants for quality of sweetness, as well as the intensity of sweetness, remain a complete mystery.

The compounds of the present invention have not previously been prepared. It has now been discovered that, surprisingly, these compounds are not only sweet and physiologically safe for oral use, but, importantly, also have adequate solubility and stability in aqueous systems. This has been discovered to be so despite the fact that a number of similar derivatives are bitter or tasteless, have serious toxicity problems, or are unstable or insoluble in water. The compounds of the present invention do not have a labile ester linkage and so are much more stable in aqueous solution than dipeptides having related structures, such as L-aspartyl-L-phenylalanine methyl ester (Aspartame ®). In addition, the amide linkage of the compounds of this invention is unexpectedly immune to enzymatic attack, so that they are not susceptible to breakdown in the gut to materials having caloric value. Finally, the preferred compound disclosed herein also has a sweetness quality equivalent to sucrose while having a sweetness intensity some 60 times greater than sucrose at an 8% sucrose sweetness level.

BACKGROUND ART

Investigations into derivatives of aspartic acid as non-nutritive sweeteners stem from the accidental discovery that L-aspartyl-L-phenylalanine methyl ester (Aspartame ®) is sweet, 130-180 times sucrose, and free of unpleasant aftertaste. R. H. Mazur, J. M. Schlatter, and A. H. Goldkamp, JACS, 91, 2684 (1969). The authors disclosed that the L-aspartic acid portion of the molecule is critical for sweetness, but that considerable modification of the phenylalanine portion could be tolerated.

Subsequent work investigated the structural relationships of aspartic acid amides as regards sweetness. R. H. Mazur, A. H. Goldkamp, P. A. James, and J. M. Schlatter, *J. Med. Chem.*, 13, 12–17 (1970). The authors' investigations attempted to delineate the structural requirements for good sweetness in alkyl amide derivatives of L-aspartic acid as revealed by tests of the following L-aspartate derivatives:

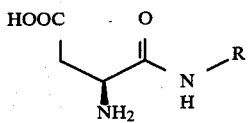

R:
  4-methylpentyl—tasteless
  1-ethylbutyl—bitter
  hexyl—sweet, 1-2 X sucrose
  heptyl—sweet, 1-2 X sucrose
  1-methylbutyl—tasteless
  1-methylpentyl—sweet, 30 X sucrose
  1-methylhexyl—sweet, 20-50 X sucrose
  1-methylheptyl—sweet, 10 X sucrose
  1,3-dimethylbutyl—bitter
  1,3-dimethylpentyl—sweet, 1-2 X sucrose
  1,4-dimethylpentyl—sweet, 50-100 X sucrose British Patent No. 1,381,826, Neely, Jan. 29, 1975, claims the use of L-aspartyl-L-1,4-dimethylpentylamide in oral compositions as a sweetener.

Y. Ariyoshi, N. Yasuda, K. Yamatani, *Bull. Chem. Soc. Japan*, 47, 326 (1974) describe investigations into the sweetness of hydroxy-substituted derivatives of L-aspartyl dipeptides. They report that both alpha-L-aspartyl-D-threo-threonine esters and alpha-L-aspartyl-D-erythro-threonine esters were sweet.

L-threonine derivatives of alpha-L-aspartic acid have no sweetness. L. B. P. Brussel, H. C. Peer, A. van der Heijden, *Z. Lebensm. Unters. Forsch.*, 159, 339 (1975).

M. Miyoshi, K. Nanami, H. Sugano, T. Fujii, *Bull. Chem. Soc. Japan*, 51, 1433 (1978) disclose L-aspartyl dipeptides of the formula:

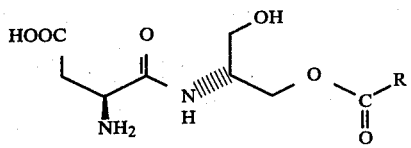

as being sweet.

Belgian Patent No. 851,368, Ferrer, May 5, 1977, disclosed the L-aspartate of 6-amino-2-methyl-2-heptanol for use in the treatment of cardiac and pulmonary insufficiency.

In the gastrointestinal tract, L-aspartyl alkaneamides and L-aspartyl-1-hydroxymethyl alkaneamides are hydrolyzed to aspartic acid and the corresponding amine by aminopeptidase enzymes. E. F. Marsh, D. A. Herring, *J. Pharm. Exp. Therapy*, 102–178 (1951) describe a study of the comparative pharmacology of hydroxyl and methyl derivatives of 1,5-dimethylhexylamine (named as 6-methyl-2-heptylamine by the authors). These compounds would be produced by the hydrolysis of the L-aspartyl dimethylhexylamide. The data show the amine compound to have vasopressor and myocardial stimulant activity. This activity is shown to be lessened somewhat by 5-hydroxyl or 2- or 3-methyl substitution. 1,5-dimethylhexylamine has been sold commercially as a vasoconstrictor (Octodrine); 1,3-dimethyl pentylamine has been sold as a vasoconstrictor (Forthane); 1,5-dimethylaminohexan-5-ol hydrochloride has been sold as a cardiac stimulant and coronary vasodilator (Heptanol).

DISCLOSURE OF THE INVENTION

The present invention encompasses compounds of the formula

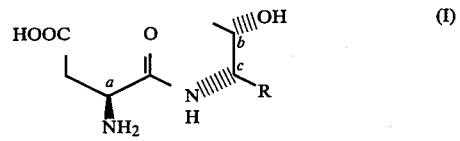

wherein R is $C_4$–$C_9$ straight, branched or cyclic alkyl, and wherein carbons a, b and c have the (S) configuration (i.e., the alkyl amino group has the threo configuration), and toxicologically acceptable salts thereof.

Especially preferred salts include the sodium, potassium, calcium, magnesium, ammonium, citrate, succinate, fumarate, phosphate, and hydrohalide salts of the foregoing compounds.

The present invention also encompasses compositions of matter comprising an ingestible carrier, i.e., food, beverage, drug, mouthwash, dentifrice, or other compositions designed for oral use, containing a sweetening amount of a compound having formula I above.

This invention arises from the discovery that these compounds have the desirable sweetness quality and intensity, solubility, caloric content and safety required of non-nutritive sweeteners.

The preferred sweetener compound herein has the formula:

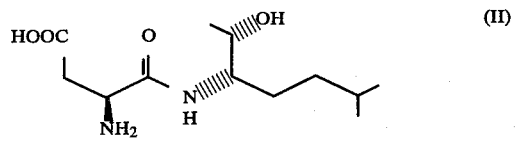

The preferred sweetener compound II is approximately 60 times as sweet as sucrose at an 8% sucrose sweetness level and has a sweetness quality comparable to sucrose. Compound II is sweet in both aqueous solution and granular form; it is stable in moderately alkaline, neutral and moderately acidic aqueous media; unlike other sweeteners of related structure, it is, unexpectedly, resistant to enzymatic hydrolysis; and it is surprisingly soluble in water, so that its sweetening power is quite high.

It will be appreciated that this compound, having three asymmetric centers, can exist in 8 possible configurations, each with potentially different taste characteristics. It has been discovered that, of these, the (S,S,S) compound is sweet.

Sweeteners of this invention are desirably used in the form of salts. Salts are preferred because they dissolve rapidly and also provide a more rapid onset of sweetness than the compounds themselves. By "toxicologically acceptable salts", as used herein, is meant salts of the instant compounds which are physiologically acceptable for ingestion.

The compounds of this invention are useful for sweetening a variety of food products such as fruits, vegetables, juices, cereals, meat products such as ham or bacon, sweetened milk products, egg products, salad dressings, ice creams and sherbets, gelatins, icings, syrups, cake mixes and frostings, as well as for sweetening beverages such as lemonade, coffee, tea, carbonated and non-carbonated soft drinks and wine. The compounds of this invention can also be used to sweeten dentifrices, mouthwashes, and chewing gums, as well as drugs such as liquid cough and cold remedies. As an alternative to direct addition of the compounds of this invention in the preparation of the foregoing compositions, sweetener concentrates can be prepared using these compounds, in granular or liquid form, for example. These concentrates can then be conveniently metered into foods, beverages, and the like, as desired by the user.

These sweetening agents are stable substances and can be used in a variety of physical forms, e.g., as powders, granules, tablets, syrups, pastes, solutions, etc. Liquid or solid carriers such as water, glycerol, starch, sorbitol, salts, citric acid, cellulose and other suitable non-toxic substances can also be used as carriers. The sweetening agents can readily be used in pharmaceutical compositions to impart a sweet taste.

The sweetening agents of this invention are used in amounts sufficient to provide a sweet taste of the desired intensity for the orally ingested composition. The amount added will generally depend upon commercial needs as well as individual sweetness sensitivities.

Some of the compounds of this invention, although sweet, are not as preferred as Compound (II) by reason of solubility or sweetness quality.

SYNTHESIS

The synthesis of the compounds of formula I is a multi-step process. Although time consuming, the process involves only standard organic synthetic techniques.

EXAMPLE 1

Synthesis of (S)-3-amino-4-[(S,S)-1-(-1-hydroxyethyl)-4-methylpentyl-amino]-4-oxo-butyric acid (Compound of formula (II))

A. Methyl N-carbobenzoxy-(2R)-amino-(3S)hydroxybutyrate

Thionyl chloride (39.0 ml, 0.542 mole) was added dropwise with stirring to 150 ml of dry methanol at $-10°$ C. Then, 17.85 g. (0.15 mole) of D(+) threonine was added, cooling was discontinued and the reaction mixture was kept at about 22° C. for sixteen hours. The mixture was evaporated in vacuo to remove the solvent plus excess thionyl chloride, leaving crude D(+) threonine methyl ester HCl in essentially quantitative yield. The ester was dissolved in 375 ml saturated aqueous sodium bicarbonate, and the solution was stirred vigorously at about 22° C. while benzyl chloroformate (25.0 ml, 0.18 mole) was added dropwise over 5 minutes. The product separated as an oil which spontaneously crystallized after about 16 hours. This product was extracted into ether and after drying over anhydrous magnesium sulfate and evaporation, 42.8 g of white solid was obtained. Recrystallization from ethyl acetate/hexane gave two crops of product: (a) 30.91 g, m.p. 89.5°–91.5° C. and (b) 3.43 g, m.p. 87°–89° C.; total yield was 71%. Analysis calculated for $C_{13}H_{17}NO_5$: C=58.42%; H=6.41%; N=5.24%. Found: C=58.50%; H=6.45%; N=5.21%.

B. Methyl N-Carbobenzoxy-(2R)-amino-(3S)-t-butoxybutyrate

A 500 ml Pyrex pressure bottle was charged with 12.12 g (0.045 mole) of the product of Step A and 90 ml of dichloromethane, and cooled to 0° C. After adding 0.9 ml concentrated sulfuric acid, isobutene was passed through the stirred, cold solution for one hour. The bottle was sealed, kept at about 22° C. for 24 hours, recooled to 0° C. and opened. The contents were poured into 150 ml of ice-cold saturated aqueous sodium bicarbonate solution. On warming to about 22° C., the excess isobutene boiled off and the residual halocarbon solution was separated, washed with brine, and dried over anhydrous $Na_2SO_4$. Evaporation of solvent in vacuo gave 13.86 g (96% yield) of product as a nearly colorless oil. This product was completely homogeneous by thin layer chromatographic analysis, and $^1$H-NMR data showed that the desired product had been obtained.

C. N-carbobenzoxy-(2R)-amino-(3S)-t-butoxybutanal

A solution containing 9.69 g (0.030 mole) of the product of Step B in 120 ml dry toluene was stirred under argon at $-60°$ C. and treated dropwise with 65.5 ml (0.0655 mole) of 1 M diisobutylaluminum hydride (in hexane). Following the 0.5 hour addition period, the mixture was kept at $-60°$ C. for 0.75 hour, and then quenched with 225 ml of 10% aqueous citric acid solution. The organic phase was separated and the aqueous phase was extracted once with ethyl acetate. The organic extracts were combined, washed with brine, and dried over anhydrous sodium sulfate. Evaporation of solvent in vacuo gave 8.67 g (99% yield) of the desired aldehyde as a nearly colorless oil, confirmed by $^1$H-NMR; purity was confirmed by thin layer chromatography. TLC showed some alcohol formation due to overreduction.

D. N-carbobenzoxy-(3S)-amino-(2S)-t-butoxy-6-methyl 4-heptane

A stirred suspension of isobutyltriphenyl phosphonium bromide (2.24 g, 0.00559 mole) in 50 ml dry THF was treated dropwise at 22° C. with 2.0 ml of 2.5 M n-butyllithium (in hexane). After stirring about 5 minutes, the mixture was cooled to 0° C. and a solution containing 0.656 g (0.00224 mole) of the product of Step C in 4 ml THF was added dropwise over 15 minutes. The mixture was stirred 1.5 hours at 0° C., then for 16 hours at about 22° C., and finally heated at reflux for 2 hours. After adding 2 ml of acetic acid, most of the THF was removed in vacuo, and 50 ml water was added and the product was extracted with ether. Upon evaporation of the dried ($Na_2SO_4$) ether solution, 1.68 g of oil was obtained which was fractionated by column chromatography on silica gel-G. Elution with benzene and 95/5 benzene-ethyl acetate gave 0.513 g of the olefinic product (68% yield) as a nearly colorless oil. Identity was confirmed by NMR data and thin layer chromatography showed an apparent mixture of E/Z geometrical isomers.

E. (3S)-Amino-(2S)-t-butoxy-6-methylheptane 0.0513 g (0.00153 mole) of the product of Step D was mixed with 0.244 g of 10% Pd/charcoal catalyst and 15 ml of methanol and stirred under 1 atm. $H_2$ for 5 hours. Filtration of catalyst followed by evaporation of solvent in vacuo gave 0.327 g of product (100% yield) as a colorless oil which gradually crystallized upon standing. Identity of the desired product was confirmed by $^1$H-NMR and purity by thin layer chromatography.

F. (S,S)-3-Amino-2-hydroxy-6-methylheptane

Freshly redistilled trifluoroacetic acid (10 ml) was added to 0.327 g (0.00163 mole) of the product of Step E, and the resulting solution was stored at 22° C. for 16 hours. Excess trifluoroacetic acid was then evaporated in vacuo and the residue was made alkaline by adding 5 ml 2 N sodium hydroxide solution. The mixture was saturated with sodium chloride and extracted with ether to separate the product. Evaporation of the dried ($Na_2SO_4$) ether solution gave 0.173 g or the desired product (73% yield) as a colorless oil. Identity was confirmed by $^1$H-NMR and purity by thin layer chromatography.

G. (S)-3-carbobenzoxyamino-4-[(S,S)-1-(1-hydroxyethyl)-4-methyl-pentylamino]-4-oxo-butyric acid-benzyl ester A solution of N-carbobenzoxy-L-aspartic acid (beta-benzyl ester), 0.927 g (0.00260 mole) in 20 ml dry THF was stirred under argon and maintained at −15° C. while 0.285 ml (0.00260 mole) N-methylmorpholine and 0.389 ml (0.0030 mole) isobutylchloroformate were added dropwise in sequence. The mixture was stirred 10 minutes and a solution containing 0.277 g (0.00191 mole) of the product of Step F in 5 ml THF was added dropwise over 10 minutes; the mixture was stirred an additional 15 minutes and then warmed to about 22° C. Evaporation of the THF gave a crude product which was treated with water and extracted with ethyl acetate. The organic phase was washed with 1 N hydrochloric acid, 5% sodium bicarbonate, brine and dried over anhydrous sodium sulfate. Evaporation of the solvent in vacuo gave 1.40 g of an oil which was fractionated by column chromatography over silica gel-G. The fraction eluted by 1:4 ethyl acetate:benzene was crystallized from ether at −10° C. to yield 0.10 g (11% yield) of white solid, m.p. 83.5°-85° C. Elemental analysis calculated for $C_{27}H_{36}N_2O_6$: C=66.92%; H=7.49%; and N=5.78%. Found: C=67.12%, 67.38%; H=7.73%; and N=5.84%, 5.76%. Structural identity was confirmed by $^1$H-NMR.

H. (S)-3-amino-4-[(S,S)-1-(1-hydroxyethyl)-4-methyl-pentylamino]-4-oxo-butyric acid—Compound (II)

A mixture containing 0.91 g (0.00188 mole) of the product of Step G, 0.5 g of a 10% Pd/charcoal catalyst, 30 ml acetic acid and 20 ml water was shaken under $H_2$ at 48 psig at 22° C. for 3.5 hours. Following filtration of the catalyst, the filtrate was evaporated to dryness and the solid product was recrystallized from methanol to afford 0.586 g (87% yield) of a white solid, m.p. 196°-197° C. dec. Structural identity was confirmed by NMR; $[\alpha]_D^{23}$ +0.63° (C, 0.959 water). Elemental analysis calculated for $C_{12}H_{24}N_2O_4$: C=55.36%; H=9.29%; N=10.76%. Found: C=55.43%; H=9.86%; and N=10.78%.

The schematic of this synthesis is depicted on the following page.

This procedure can be readily modified to provide the various salts, esters, and the like disclosed hereinabove. In addition, selection of an appropriate aralkyl phosphonium bromide reagent in Step D is all that is necessary to produce the close alkyl analogs of the preferred compound described above.

The various solvents, reagents and techniques used in the foregoing synthetic procedures are well known and within the synthetic chemist's armamentarium.

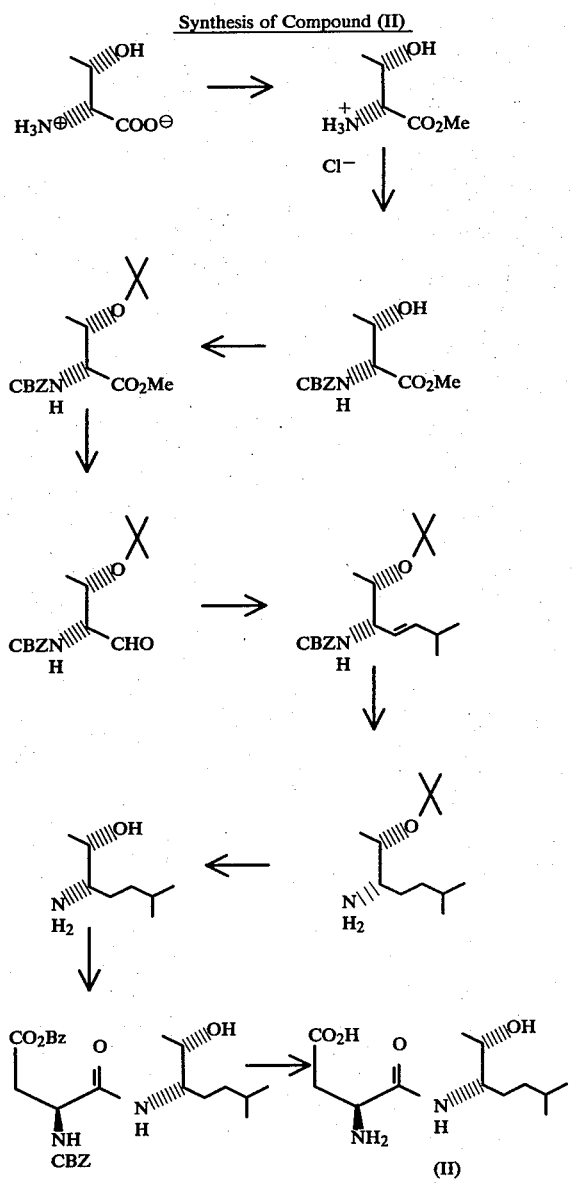

Synthesis of Compound (II)

EXAMPLE 2

Sweetness and Sweetening Power

Taste Evaluation Procedure

The taste quality and sweetness intensity of the compounds of the present invention were determined by the following procedure.

Male subjects were selected at random from a group of about 20 persons who had previously been selected on the basis of proven tasting acuity, i.e., persons who could easily recognize the four basic tastes (sweet, sour, bitter and salty) and who were adept at quantifying their own physiological response numerically. The subjects were asked to taste and expectorate about 10 ml of a sample at about 22° C. containing dissolved test material. The subjects were then asked to compare the sweetness (and other taste qualities) of the test solution with four or five standard coded samples which contained increasing amounts of sucrose. Sweetness intensity of the unknown material was recorded by the subject making a mark on a coded closed linear scale at a point he considered equal in sweetness among the standards; interpolation between standards was encouraged. After completion of the panel, a four or five point (1–4 or 1–5, depending on the number of standards) numeric scale was superimposed on the coded linear scales to obtain numerical data; data were averaged and recorded to the nearest 0.25 unit. Equivalent sucrose sweetness was determined by referring to graphs of (w/v) sucrose concentration and standards versus a linear numeric scale.

Sweetness intensity was calculated by dividing the concentration (w/v) of perceived sweetness by the concentration (w/v) of test material required to produce that sweetness. Most taste comparisons were made in the range of 5–10% sucrose sweetness.

The five point scale with standards ranging from 1.37% (0.040 M) to 11.97% (0.35 M) sucrose usually sufficed to bracket the sweet intensity of a test sample. However, in the cases of beverage prototypes it was more meaningful to use prototype beverage solutions containing 2.5, 5.0, 10.0, 15.0 and 20.0% sucrose as standards. In all cases, evaluation of sweetness intensity in terms of sucrose equivalents was made with reference to graphs which related sucrose concentration and standard prototypes to the particular (arbitrary) scale units employed.

In tests in which taste quality was estimated, the subjects were asked to describe the initial taste and aftertaste in terms of percent sweet, sour, bitter, salty and "other", totalling 100%. In all tests, bottled spring water was used for rinsing between samples. The results for the compounds of the present invention are shown in the following table.

| Taste Properties of Representative Compounds | | |
|---|---|---|
| Compound | Medium | Sweetness Intensity (× sucrose) |
| 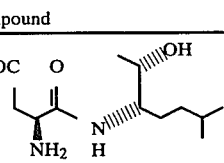 | Water Lemonade | 60× 85× |

| Taste Properties of Representative Compounds | | |
|---|---|---|
| Compound | Medium | Sweetness Intensity (× sucrose) |
| 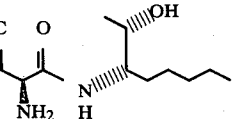 | Water | 35× |

No significant off-tastes were noted.

Solubility and Sweetening Power

The solubility of compound (II) was determined in standard fashion. Water at pH 7 and 20° C. was used, except where indicated.

| Compound | Aqueous Solubility g % | Calculated Maximum Effective Sweetening Power, g % sucrose equivalent |
|---|---|---|
| (II) | ~3–4 | ~180–240 |
| (II), lemonade | " | ~255–340 |

Because sweetness tends to plateau at higher concentrations of high intensity sweeteners, these calculations overestimate the actual sweetening power of the compounds of this invention. However, it can be seen that these compounds possess ample sweetening power for use in foods, beverages, and other oral products.

EXAMPLE 3

Hydrolytic Stability

Stability tests were performed on the compound of formula (II) to determine the sweetener's resistance to hydrolysis under varying conditions.

The tests were performed using solutions of (II) in aqueous phosphate buffer, 0.02 M, at pH 3.5 and 6.9. The solutions were incubated at ~43° C. (110° F.), ~54° C. (130° F.), and ~66° C. (150° F.) for up to 32 days.

Samples from the test solutions were withdrawn at regular intervals and analyzed by reversed-phase high performance liquid chromatography for remaining intact (II), using the following conditions:

Column: 25 cm×0.4 cm I.D. stainless steel packed with Lichrosorb RP-18, 5μ particle size.

Mobile phase: Acetonitrile/0.01 M phosphate buffer (155/845 v/v), pH 6.

Flow rate: 1.5 ml/min.

Detection: UV absorbance at 220 nm (~2200 Å). Results were quantified by comparison with standard solutions kept frozen during the tests. Peak heights were measured for replicate injections.

The results are depicted in Table I.

TABLE I

| Temperature, °C. (°F.) | pH start (end) | Half-life, days |
|---|---|---|
| 43 (108 ± 1) | 3.5 (5.2) | No detectable decomposition |

TABLE I-continued

[Chemical structure: HOOC-CH(NH₂)-C(=O)-N(H)-CH(CH₂CH(CH₃)₂)-OH shown with stereochemistry]

| Temperature, °C. (°F.) | pH start (end) | Half-life, days |
|---|---|---|
| | | after 32 days |
| | 6.9 (6.8) | 148 |
| 54 (129 ± 1) | 3.5 (4.3) | 57 |
| | 6.9 (6.09) | 64 |
| 66 (151 ± 7) | 3.5 (4.8) | 17 |
| | 6.9 (7.5) | 22 |

Considerable pH drift was experienced at pH 3.5 due to the limited capacity of the buffer system. Less drift was found at pH 6.9.

When log (% (II) intact) is plotted versus time, the resulting linear function is consistent with a reaction following first order kinetics.

By use of the Arrhenius equation, $$\frac{d(\ln)k}{dt} = \frac{A}{RT^2},$$

where k is the specific reaction velocity, T is the absolute temperature (°K.), A is the activation energy constant, t is time, and R is the gas law constant, change in the rate of a first-order chemical reaction with temperature can be calculated. The half-life of (II) at ambient temperature and pH 6.9 is estimated to be 760 days (>2 yrs).

Table II indicates comparable test data for Aspartame ® (L-aspartyl-L-phenylalanine methyl ester), published by G. D. Searle & Co., illustrating the marked superiority in resistance to hydrolysis of the present compounds, compared to an art compound currently under commercial development.

TABLE I

[Chemical structure: Aspartame — HOOC-CH(NH₂)-C(=O)-N(H)-CH(CH₂-C₆H₅)-COOCH₃]

Aspartame ® Stability

| Temperature, °C. | pH | Half-Life, Days |
|---|---|---|
| 40 | 4 | 68 |
| | 7 | 0.16 (3.9 hours) |
| 55 | 4 | 16 |
| | 7 | 0.05 (1.2 hours) |

Table III expresses the stability data differently, indicating % active (sweet) compound remaining. Again, the hydrolytic superiority of compounds of this invention can be seen.

TABLE III

Aspartic Acid Derivative Sweeteners

| Compound | % Remaining After 15 Days in .02M Phosphate Buffer at 54° C. | |
|---|---|---|
| | pH 3.5 | pH 7 |
| [Structure: HOOC-CH(NH₂)-C(=O)-N(H)-CH(CH₂CH(CH₃)₂)-OH with stereochemistry] | 82% | 86% |
| *[Structure: HOOC-CH(NH₂)-C(=O)-N(H)-CH₂-CH₂CH(CH₃)₂ with OH] | 88% | 72% |
| [Structure: HOOC-CH(NH₂)-C(=O)-N(H)-CH(CH₂-C₆H₅)-COOCH₃] Aspartame ® | 50%** | 0**(at 1 day) |

*(Described in application of L. M. Brand, S.N. 972,093, filed Dec. 21, 1978.)
**comparable data from literature

EXAMPLE 4

Resistance to Hydrolysis by Digestive Enzymes

Published studies have indicated that Aspartame ® and related alpha-amides of L-aspartic acid are readily converted to L-aspartic acids by enzymes in the gut. This aspartic acid has the same caloric value as sugar, on a per-gram basis. These aspartic acid amide sweeteners are therefore not non-nutritive, but, rather, low calorie. In addition, the other molecular fragment released as a result of amide cleavage is frequently a non-physiological amine. It was therefore considered appropriate to gauge the rate of amide cleavage of compound (II) by digestive enzymes in evaluating both the calorigenic and the toxicologic potential of compounds of this invention.

Assays were performed in the following manner:

Aliquots of four mM solutions of test compounds in 100 mM potassium phosphate buffer solution at pH 7.0 were incubated at 37° C. (98.6° F.) for up to two hours with a standardized amount of animal intestine homogenate containing digestive enzymes. At the end of the incubation period, the enzymes were inactivated by boiling and the extent of amide bond hydrolysis was quantified by measurement of free L-aspartic acid in the solution. This was done by incubating a sample of the test solution with enzymes and substrates that convert L-aspartate to L-malate with concomitant oxidation of a pyridine nucleotide having a characteristic absorbance at 340 nanometers. The decrease in optical density at this wavelength is proportional to the amount of L-aspartate generated by amide bond hydrolysis.

Table IV lists the structures of various aspartic acid amides and the relative rates of hydrolysis by animal intestine homogenizates obtained from species with digestive processes similar to that of man. Results have been standardized to 100 using L-aspartyl-L-phenylalanine (Aspartame ®) and rat digestive enzymes as standards. The results indicate the remarkable and unexpected resistance to enzymatic attack exhibited by the compounds of the present invention. Thus they appear to be non-nutritive, unlike other aspartic acid amide sweeteners. These results also indicate that the (S,S,S) configuration is as essential to enzyme resistance as to sweetness.

TABLE IV

| Structure | Relative rate of amide bond cleavage | |
|---|---|---|
| | Rat Intestine | Monkey Intestine |
| HOOC-...-COOCH₃ (benzyl) | 100 | 157 |
| HOOC-...-OH (benzyl) | 19 | n.t.* |
| HOOC-...-OH (isobutyl) | 11 | n.t. |
| HOOC-...-OH (isopentyl) | 35 | 103 |
| HOOC-...-OH (hexyl) | 35 | n.t. |
| HOOC-...-(isohexyl) | 38 | 68 |
| HOOC-...-(naphthyl) | 4 | n.t. |
| HOOC-...-OH (isopentyl, ethyl) | 0 | 0 |
| Compound II | | |
| HOOC-...-OH (isopentyl) | 41 | n.t. |
| HOOC-...-OH (hexyl) | 0 | 0 |

*not tested

INDUSTRIAL APPLICABILITY

EXAMPLE 5

The following structures illustrate compounds within the scope of this invention without intending to be limitative thereof. It should be understood that:

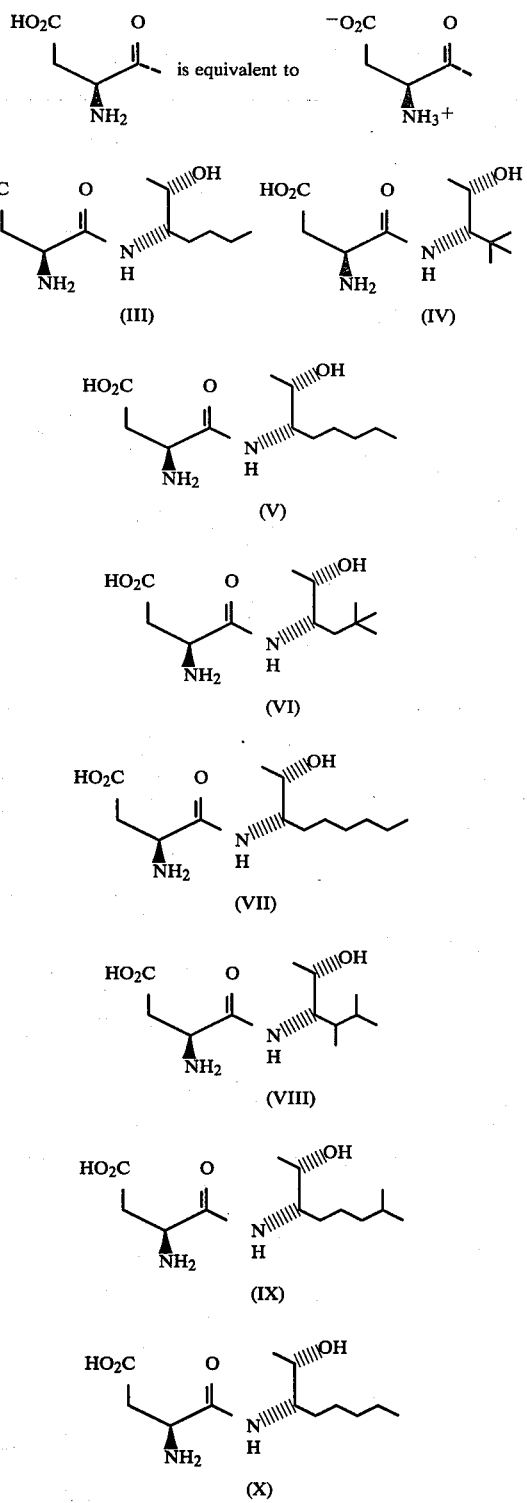

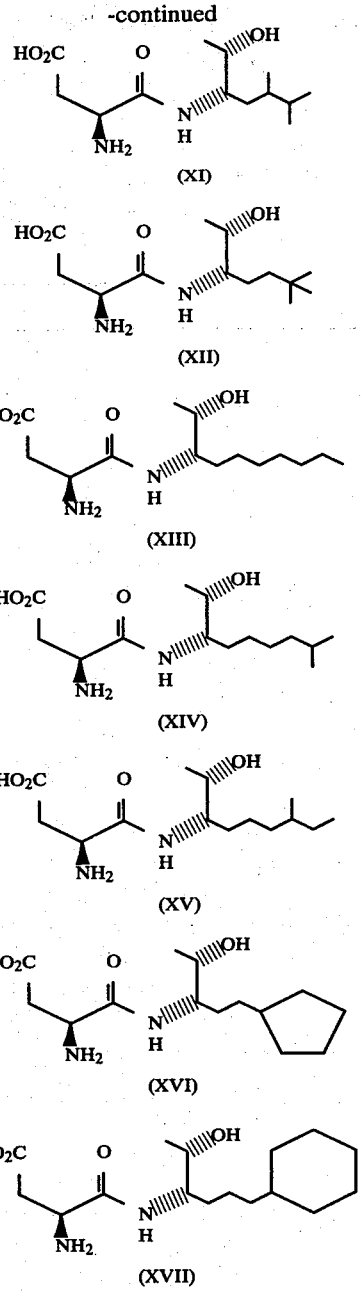

EXAMPLE 6

Orange Carbonated Beverage

A stock supply of bottlers' syrup is prepared by mixing 5.5 liters (l.) of a 50% aqueous citric acid solution with 150 l. of water, dissolving 1 kg. of Compound (II) in that solution, adding successively 7.02 l. of the orange flavor base FO-78 manufactured by A. E. Illes, Dallas, Tex., and 2.7 kg. of sodium benzoate, and diluting that mixture to 200 l. with water.

Sixty milliliter (ml.) aliquots of the foregoing syrup in 12 oz. cans are diluted with 215 ml. cold tap water per can, and 80 ml. cold charged bottling water (5 vol. $CO_2$) per can are added to provide carbonation. The cans are sealed and the contents are mixed.

When the Compound (II) is replaced with an equivalent sweetening amount of one or more of the compounds of Example 5, the resulting composition is also within the scope of the invention.

EXAMPLE 7

The following toothpaste formulation is within the scope of this invention:

| Ingredient | Wt. % |
|---|---|
| Calcium pyrophosphate | 40.00 |
| Sorbitol (70% aqueous solution) | 20.40 |
| Glycerine | 10.20 |
| Sodium coconut monoglyceride sulfonate | 0.80 |
| Sodium carboxymethyl cellulose | 1.20 |
| Sodium coconut alkyl sulfate (20% active) | 2.30 |
| Sodium fluoride | 0.22 |
| Sweetener (Compound (III)) | 0.40 |
| Flavor | 0.90 |
| Red urea formaldehyde agglomerates | 0.65 |
| Water and minor ingredients | Balance to 100 |

When the sweetener is replaced by an equivalent sweetening amount of one or more of the other compounds of Example 5, the resulting toothpastes are also within the scope of this invention.

EXAMPLE 8

A mouthwash according to this invention is prepared by co-dissolving the following ingredients:

| Ingredient | Percent by Weight |
|---|---|
| Glycerine | 10.00 |
| Ethyl alcohol | 17.00 |
| Cetyl pyridinium chloride | 0.05 |
| Sorbitan monooleate polyoxyethylene | 0.13 |
| Flavor (Oil of Wintergreen) | 0.09 |
| Sweetening agent* | 0.5 |
| Water and minor ingredients | Balance |

*Compound (VI), Hydrochloride salt

The sweetening agent can be replaced with an equivalent sweetening amount of (S)-3-amino-4-[(S,S)-1-(-1-hydroxyethyl)-heptanylamino]-4-oxo-butyric acid (VII)

EXAMPLE 9

A gel dentifrice having the following formulation is prepared by conventional means:

| Ingredients | Percent by Weight |
|---|---|
| Silica xerogel | 12.00 |
| Silica aerogel | 5.00 |
| Hydroxyethyl cellulose | 1.50 |
| Glycerine | 34.76 |
| Stannous fluoride | 0.41 |
| Flavor (Wintergreen) | 0.95 |
| Color (FD & C Blue #1) | 0.03 |
| 21% sodium lauryl sulfate-79% glycerine mixture | 6.00 |
| Sweetener* | 0.30 |
| Water and minor ingredients | Balance |

The above composition is prepared by blending and deaerating the listed ingredients in standard fashion.
*Compound of formula (V), Calcium salt.

EXAMPLE 10

A liquid cough remedy is prepared by conventional means:

| Ingredients | |
|---|---|
| Dextromethorphan HBr | 150 mg |
| Citric acid | 800 mg |
| 90% Ethanol | 6 ml |
| Sweetener solution (prepared by adding purified water to 13 g compound (IX) of Example 5 to a total of 1000 g) | to 50 ml |

The composition is prepared by mixing the dextromethorphan and the citric acid separately in 0.3 ml portions of the 90% ethanol, mixing the two portions of ethanol together, and combining the dextromethorphan/citric acid/ethanol mixture with the sweetener solution.

EXAMPLE 11

A chewing gum is prepared by replacing the sucrose normally added to chewing gum with the sweeteners of the instant invention. A gum base is prepared from:

| Ingredients | Weight in Grams |
|---|---|
| 60% latex | 18 |
| Hydrogenated rosin esters | 44 |
| Paracumarine resin | 7.5 |
| Candellila wax | 6 |
| Glyceryl tristearate | 2.5 |
| Ethyl cellulose | 2 |
| Calcium carbonate | 20 |

The aforesaid gum base is used with the sweeteners of this invention to prepare a chewing gum having a greatly reduced sugar content.

| | Percent by Weight |
|---|---|
| Gum base | 68 |
| Sweetener* | 15 |
| Corn syrup | 16 |
| Flavor | 1 |

*Compound (X)

Chewing gum can also be prepared using other compounds of this invention.

EXAMPLE 12

Powdered Sweetener Concentrate

| Compound (II) HCl | 160 mg. |
|---|---|
| Dextrose | 840 mg. |

One packet containing the foregoing ingredients will be the approximate equivalent of two teaspoons of sugar.

EXAMPLE 13

Liquid Sweetener Concentrate

| | Gm. % |
|---|---|
| Compound (II) HCl | 3 |
| Benzoic acid | 0.1 |
| Methyl paraben | 0.05 |
| Water | q.s. |

Ten drops provides the approximate sweetening power of one teaspoon of sugar.

What is claimed is:

1. A compound of the formula:

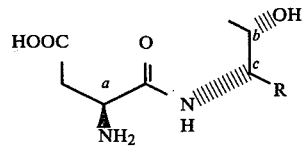

wherein R is isopentyl, and wherein carbons a, b and c have the (S) configuration, and toxicologically acceptable salts thereof.

2. The sodium, potassium, calcium, magnesium, ammonium, citrate, succinate, fumarate, phosphate or hydrohalide salt of the compound of claim 1.

3. A composition of matter for oral ingestion comprising a sweetening amount of a compound or salt according to claim 1, and an ingestible carrier.

4. A food or beverage according to claim 3.

5. A food or beverage according to claim 4 wherein R is isopentyl.

6. A carbonated beverage according to claim 5.

7. An orange flavored beverage according to claim 5.

8. A cola-flavored beverage according to claim 5.

9. A lemon, lime, or lemon-lime flavored beverage according to claim 5.

10. A lemonade-type beverage according to claim 4.

11. A liquid sweetener according to claim 3, wherein the carrier is water.

12. A sweetener according to claim 11 wherein the compound is present at a concentration of from 0.02% to about 12%.

13. A dentifrice composition containing a sweetening amount of a compound or salt according to claim 3.

14. A non-cariogenic mouthwash according to claim 13.

15. A non-cariogenic toothpaste according to claim 13.

16. A method of sweetening compositions for oral ingestion without significantly increasing their caloric content, comprising adding to the compositions a sweetening amount of a compound or salt according to claim 1.

* * * * *